US007699992B2

(12) United States Patent
Sternby

(10) Patent No.: US 7,699,992 B2
(45) Date of Patent: Apr. 20, 2010

(54) METHOD AND APPARATUS FOR DETERMINING A PATIENT OR TREATMENT OR APPARATUS PARAMETER DURING AN EXTRACORPOREAL BLOOD TREATMENT

(75) Inventor: Jan Peter Sternby, Lund (SE)

(73) Assignee: Gambro Lundia AB (SE)

( * ) Notice: Subject to any disclaimer, the term of this patent is extended or adjusted under 35 U.S.C. 154(b) by 917 days.

(21) Appl. No.: 11/013,783

(22) Filed: Dec. 17, 2004

(65) Prior Publication Data
US 2005/0133449 A1 Jun. 23, 2005

Related U.S. Application Data

(60) Provisional application No. 60/531,280, filed on Dec. 18, 2003.

(51) Int. Cl.
*B01D 61/00* (2006.01)
*B01D 61/24* (2006.01)
*B01D 61/32* (2006.01)
*B01D 61/30* (2006.01)

(52) U.S. Cl. ............ 210/739; 210/96.2; 210/143; 210/645; 210/646; 210/740; 210/741; 210/745; 210/746

(58) Field of Classification Search ............ 210/645, 210/646, 739, 740, 741, 742, 743, 744, 745, 210/746, 96.2, 143; 604/65, 67
See application file for complete search history.

(56) References Cited

U.S. PATENT DOCUMENTS

| 4,923,613 | A | 5/1990 | Chevallet |
| 4,990,258 | A * | 2/1991 | Bjare et al. ............ 210/647 |
| 5,024,756 | A | 6/1991 | Sternby |
| 5,567,320 | A | 10/1996 | Goux et al. |
| 6,110,384 | A | 8/2000 | Goux et al. |
| 6,156,002 | A | 12/2000 | Polaschegg et al. |
| 6,187,199 | B1 | 2/2001 | Goldau |
| 6,258,027 | B1 | 7/2001 | Sternby |

FOREIGN PATENT DOCUMENTS

EP 0 330 892 9/1989

* cited by examiner

*Primary Examiner*—John Kim
(74) *Attorney, Agent, or Firm*—Finnegan, Henderson, Farabow, Garrett & Dunner L.L.P.

(57) ABSTRACT

During a dialysis treatment carried out by a dialysis apparatus, in which a dialysis liquid is circulated to a clean dialysate filter (43) arranged before a dialyser (3), the conductivity of the dialysis liquid is altered according to an altering function that is a function of a mathematical model of the filter (43), in a way that will make the conductivity after the filter change more quickly. A conductivity cell (47), which is arranged after the dialyser, measures the conductivity of the spent dialysis liquid changed in response to said alteration. A control and computer system (52) evaluates the dialysance from said measured response. The conductivity can be changed for a comparatively short time period that is sufficient to allow reliable results.

24 Claims, 8 Drawing Sheets

Figure 1
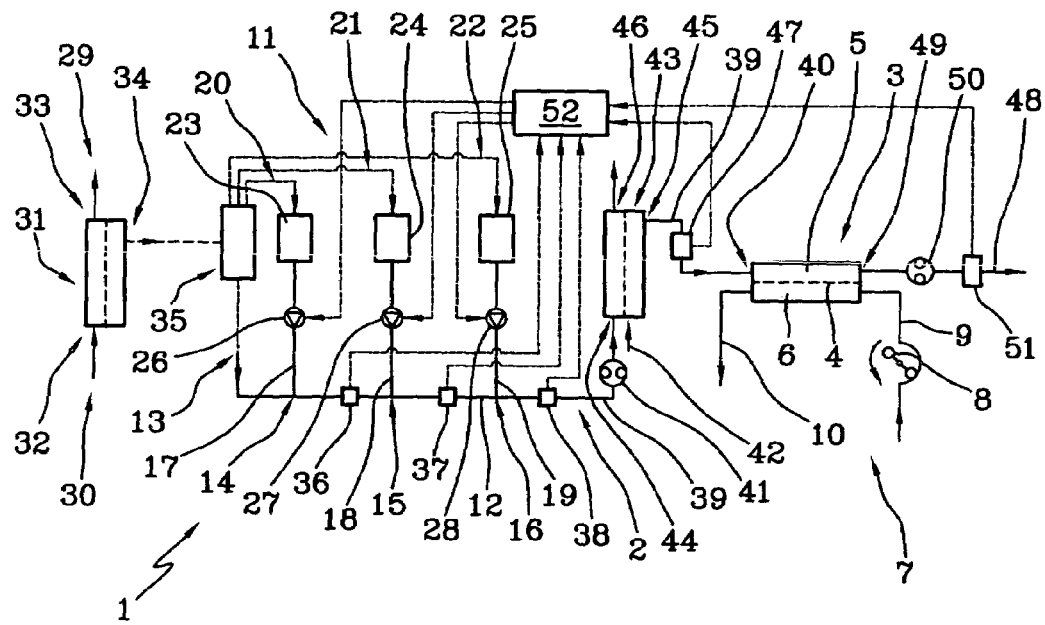
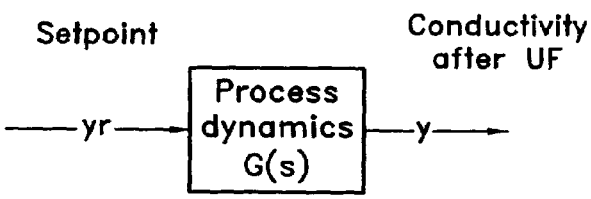
Figure 2
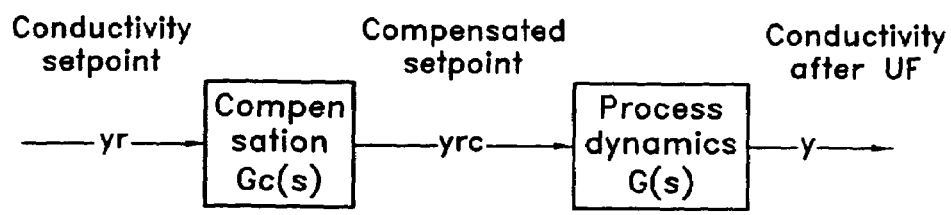
Figure 3

Figure 4  $Q_0$ =500ml/min: (a) No compensation (b) T=55, N=3

Figure 5    $Q_0 = 500$ ml/min:  (a) T=30, N=3  (b) T=55, N=6

Figure 6    $Q_0 = 300$ml/min: (a) No compensation (b) T=55, N=3

Figure 7    $Q_0$ =900ml/min: (a) No compensation  (b) T=20, N=3

METHOD AND APPARATUS FOR DETERMINING A PATIENT OR TREATMENT OR APPARATUS PARAMETER DURING AN EXTRACORPOREAL BLOOD TREATMENT

CROSS REFERENCE TO RELATED APPLICATION

This application claims the benefit of U.S. Provisional Application No. 60/531,280, filed on Dec. 18, 2003, the contents of which are incorporated herein by reference.

BACKGROUND OF THE INVENTION

The invention relates to a method and to an apparatus for determining at least one patient or treatment or apparatus parameter during an extracorporeal blood treatment carried out in an extracorporeal blood treatment apparatus.

Specifically, though not exclusively, the invention can be usefully applied in dialysis treatments.

The parameters to be determined can be, for example, ionic dialysance or clearance, plasma conductivity, plasma sodium concentration, dialysis dose, depurated volume of patient body water, ionic mass balance, blood recirculation, fistula flow, etc.

During a dialysis treatment, it is desirable to monitor patient or treatment or apparatus parameters in order, for example, to provide a measure of treatment efficacy, preferably in a real time, non-invasive and automatic mode.

Several methods have been suggested for monitoring a dialysis therapy based, for example, on conductivity measurements of treatment fluids flowing in the extracorporeal blood treatment apparatus.

EP 0 291 421 discloses a method for determining the blood sodium level of a patient whose blood circulates through one compartment of an exchanger separated from a dialysis fluid by a semipermeable membrane; the conductivity of the dialysis fluid of equilibrium with the plasma is determined by: changing in a selected manner the conductivity of the dialysis fluid at inflow the exchanger, measuring the conductivity of the dialysis fluid at outflow from the exchanger, determining a lag time tL of the change in conductivity of dialysis fluid between inflow to and outflow from the exchanger, and determining an equilibrium conductivity value of the dialysis fluid for which the conductivity at outflow from the exchanger at an instant t is equal to the conductivity at inflow at an instant t-tL.

EP 0 330 892 describes a dialysis system comprising means for the conducting of dialysis liquid and blood respectively on either side of one or more membranes in a dialyzer, means for controlling one or more parameters of the dialysis liquid before the dialyzer, means for measuring at least one parameter of the dialysis liquid after the dialyzer, and means for a comparison of the parameter measured after the dialyzer with the set value of the corresponding parameter before the dialyzer; the values measured are used for the calculation of a blood parameter, which is altered as a function of the parameter measured, for the purpose of calculation and/or control of this blood parameter.

In the method disclosed in U.S. Pat. No. 6,156,002 for measurement of mass and energy transfer parameters (clearance and dialysance) in hemodialysis, a pre-determined amount of a substance whose dialysance is to be measured is added upstream of the dialyzer; the amount of substance not dialyzed in the dialyzer is measured downstream of the dialyzer by integrating the concentration over time; dialysance is calculated from the amount added upstream, the amount measured downstream and the dialysate flow; in case the substance is part of the dialysate the base concentration is subtracted during integration; the addition of the concentrate upstream of the dialyzer can be done manually or, alternatively by the mixing pump of the dialysis machine; instead of an increase of the concentration with a concentrate dilution with water can be used as well.

U.S. Pat. No. 6,187,199 shows a method for determining hemodialysis parameters during an extracorporeal blood treatment according to which the blood to be treated in an extracorporeal circulation flows through the blood chamber of a dialyzer divided by a semipermeable membrane into the blood chamber and a dialysate chamber, and dialysate in a dialysate path flows through the dialysate chamber of the dialyzer; the hemodialysis parameter can also be determined when no balanced state has yet been established; the method is based on the response of the dialyzer to a pulse function as inlet signal (pulse response) from the course over time of the physical or chemical characteristic quantity of the dialysate upstream and downstream of the dialyzer; the hemodynamic parameter is then determined from the pulse response of the dialyzer.

EP 0 920 877 provides a method for determining a parameter indicative of the effectiveness of an extracorporeal blood treatment carried out using a membrane exchanger, wherein the method includes the steps of flowing through the exchanger a treatment liquid having a concentration characteristic and of varying the value of the characteristic upstream of the exchanger for a time at the end of which the characteristic is returned to a nominal value; a plurality of values adopted by the characteristic downstream of the exchanger in response to the upstream variation is measured and stored in memory; the area of a downstream perturbation region is determined, which is bounded by a baseline and a curve representing the variation of the measured values with respect to time; then, the parameter indicative of the effectiveness of the treatment is calculated using the area beneath the upstream curve and an area beneath an upstream curve.

EP 0 658 352 makes available a method for determining a significant parameter of the progress of an extracorporeal blood treatment carried-out using a membrane exchanger, includes the steps of successively circulating three treatment fluids through the exchanger; each fluid has a characteristic linked to at least one of the significant parameters of the treatment; the value of the characteristic in the first fluid upstream of the exchanger is different from the value of the characteristic in the second fluid upstream of the exchanger, the latter being itself different from the value of the characteristic in the third fluid upstream of the exchanger; two values for each of the three treatment fluids are measured, respectively upstream and downstream of the exchanger, and at least one value of at least one significant parameter of the progress of the treatment is calculated from the measured values. This method is directed to determine the representative parameters of the progress of the treatment without, as a result, the patient having to be subjected for a long period to treatment conditions different from the prescribed conditions. This method permits a precise determination of the significant parameters of the progress of the treatment from measurements carried out at short time intervals. In this manner, the patient is exposed for only a very short time to a treatment fluid different from the prescribed treatment fluid (for example too high or too low in sodium) and the method can be carried out as often as necessary for an appropriate monitoring of the treatment session.

The prior art comprises a monitoring system, applied on a dialysis machine, which periodically measures the dialysis liquid conductivity at the dialyzer outlet, following a driven increment of the dialysis liquid conductivity at the dialyzer inlet. A processor receives said conductivity measurements and computes, by means of a mathematical model, several parameters relevant to the dialysis process, as ionic dialysance, plasma conductivity, kT/V, etc.

More in detail, for the measurement of ionic dialysance, a step increment is generated in the inlet conductivity by raising the conductivity by 1.0 mS/cm for 2 minutes and then reverting to the original conductivity. These 2 minutes have so far been sufficient to allow both the inlet conductivity and the outlet conductivity after the dialyzer to stabilize on the new level before going down again. It has thus been possible to find out the steady state level of the outlet conductivity that corresponds to each of the two inlet levels, which is used for the calculation of ionic dialysance.

With increasing demands on the quality of the dialysis fluid it has now become standard practice to offer machines that can clean the fresh dialysis fluid just before the dialyzer. The filter used for this (clean dialysate filter or ultrafilter) has to be fairly large to handle the flow of dialysis fluid, which can in some machines be up to 1000 ml/min. A large filter in the dialysis line creates an extra time period for stabilizing the outlet conductivity after the dialyzer, this extra delay in the response created by the clean dialysate filter being on top of the delay already created by the dialyzer, whereby 2 minutes may no longer be sufficient to allow reliable results. The large fluid volume in the clean dialysate filter acts as a mixing chamber that creates a very sluggish conductivity response after the filter. If the clean dialysate filter has, for example, a time constant of approximately 1 min (at 500 ml/min flow), it will correspond to a rise time (10-90%) of about 2 minutes, which is approximately equal to the duration of the afore mentioned conductivity setpoint step increment. Thus there is no chance to reach steady state conditions during the elevated conductivity period.

One solution to the problem with long time periods would be to increase the length of the conductivity step increment.

This would have several disadvantages.

One immediate disadvantage is that the mean conductivity in the inlet fluid will be changed, especially if, as normal, measurements are performed every 15 or 30 minutes. The treatment would no longer be performed with essentially constant conductivity, and the prescribing doctor might view this as a limitation.

Another disadvantage arises when the above-described monitoring system is combined with conductivity profiling, since profiling has to be prevented during and around the conductivity step increment very little time would be left for conductivity profiling.

Finally, the measurement accuracy would be decreased by the change in blood conductivity that would occur during such a long step, since changes in the blood conductivity affect the outlet conductivity.

SUMMARY OF THE INVENTION

An aim of the present invention is to make available a system for determining patient and/or treatment and/or apparatus parameters during an extracorporeal blood treatment, which overcomes all of the above-described limitations and drawbacks.

A further aim of the invention is to provide a reliable system for determining patient and/or treatment and/or apparatus parameters during an extracorporeal blood treatment, which enables the deviations from the doctor's prescription to be reduced to a minimum.

A further aim of the invention is to make available a system for determining patient and/or treatment and/or apparatus parameters during an extracorporeal blood treatment, wherein a physical or chemical characteristic of a liquid upstream a filter can be changed for a comparatively short time period that is sufficient to allow reliable results.

A further aim of the invention is to make a physical or chemical characteristic of a liquid downstream a filter change and assume a new steady state as quickly as possible.

A further aim of the invention is to make available a real time, non-invasive and automatic measure of dialysis efficacy, which is in particular suitable for dialysis apparatus wherein the fresh dialysis liquid is filtered just before the dialyzer.

A further aim of the invention is to provide a reliable system for determining patient and/or treatment and/or apparatus parameters during an extracorporeal blood treatment, that enables a physical or chemical characteristic, for example conductivity, of a liquid after the ultrafilter, and/or after the dialyzer, to be changed more quickly.

An advantage of the invention is to provide indicative values of the efficiency of the extracorporeal blood treatment, simply, automatically, using devices (such as for example conductivity transducers and concentrate pumps), which are normally already present in machines for extracorporeal blood treatment.

A further advantage is that the invention enables monitoring of the efficiency of the extracorporeal blood treatment at any time during the treatment.

These and other aims and advantages, which shall be evident in the course of the present description, are basically achieved by an invention as described in the appended claims.

According to the invention, during an extracorporeal blood treatment at least one physical or chemical characteristic of a first liquid flowing towards a portion of an extracorporeal blood treatment apparatus is altered in accordance with an altering function which is a function of a mathematical model of at least a part of said apparatus portion, at least one physical or chemical characteristic of a second liquid flowing from said apparatus portion changing in response to said alteration of said first liquid characteristic, at least one value of said second liquid characteristic being measured and used for computing at least one patient or treatment or apparatus parameter.

According to an embodiment of the invention, said mathematical model is selected so as said altering function comprises a dynamic compensation that takes into account the process dynamics of said apparatus portion in order to reduce the settling time of said response.

According to an embodiment of the invention, the mathematical model comprises an inverse of a transfer function that describes how the second liquid characteristic changes in response to an alteration of the first liquid characteristic. The order of the transfer function may be one or greater than one.

According to an embodiment of the invention, the altering function is calculated during the operation of the apparatus, or is precalculated before it, as a function of at least two transfer functions one of which has a time constant smaller than the other one. The order of each transfer function may be one or greater than one.

According to an embodiment of the invention, the altering function is calculated or precalculated as a function of a quotient of two transfer functions, the function at the numerator having a time constant smaller than the function at the denominator. The order of each transfer function may be one or greater than one.

According to an embodiment of the invention, the altering function is a function of an uncompensated function having at least a part in which the first liquid characteristic is essentially constant, and of a compensating function comprising a quotient of two transfer functions in which the function at the numerator has a time constant smaller than the function at the denominator. The order of each transfer function may be one or greater than one.

According to an embodiment of the invention, the mathematical model is selected during the operation of the apparatus, or is preselected before it, and the altering function is determined during the operation of the apparatus, or is predetermined before it, as a function of said mathematical model.

According to an embodiment of the invention, one or more mathematical models of one or more parts of an extracorporeal blood treatment apparatus are pre-stored in a computer memory, at least one part of an apparatus portion included in the apparatus carrying out the treatment is identified, at least one of the pre-stored mathematical models is associated to the identified part of the apparatus portion, and the altering function is determined as a function of said mathematical model.

According to an embodiment of the invention, the altering function is a function of a mathematical model of at least one volume that is arranged in a flow system of said apparatus portion and that slows down the response to an alteration of the first liquid characteristic. This volume could be, for example, a filtering system.

According to an embodiment of the invention, the altering function is a function of a mathematical model of at least one fluid treatment unit, the treatment fluids upstream and downstream the fluid treatment unit being the first and, respectively, the second liquid.

According to an embodiment of the invention, the altering function is a function of a mathematical model of a blood treatment unit, a fresh treatment fluid upstream the blood treatment unit and a spent treatment fluid downstream the blood treatment unit being the first and, respectively, the second liquid.

According to an embodiment of the invention, the altering function is a function of a mathematical model of a fluid treatment unit arranged before a blood treatment unit or of the blood treatment unit or of both said units, the first liquid being a treatment fluid upstream the fluid treatment unit, the second liquid being a treatment fluid downstream the fluid treatment unit and upstream the blood treatment unit or a spent treatment fluid downstream the blood treatment unit.

According to the invention, during an extracorporeal blood treatment at least one physical or chemical characteristic of a first liquid flowing towards a portion of an extracorporeal blood treatment apparatus is altered in accordance with an altering function, at least one physical or chemical characteristic of a second liquid flowing from said apparatus portion changing in response to said alteration of said first liquid characteristic, at least one value of said second liquid characteristic being measured and used for computing at least one patient or treatment or apparatus parameter, the altering function comprising at least: a first time period in which the first liquid characteristic varies with an average variation over time having a first value different from zero and regarded as positive; after the first time period, a second time period in which an average variation over time of the first liquid characteristic has a second value smaller than the first value ("smaller" means that a comparison is done considering not only the absolute values of the variations over time but also whether the variations are positive or negative); after the second time period, a third time period in which an average variation over time of the first liquid characteristic has a third value smaller than the first value and greater than the second value ("smaller" and "greater" means that comparisons are done considering not only the absolute values of the variations over time but also whether they are positive or negative). In short, the derivative of the first liquid characteristic is positive during the first period, is "smaller" (with sign) during the second period, and is in between during the third period.

According to an embodiment of the invention, the first time period is shorter than the second time period or is shorter than the third time period or is shorter than both the second and the third time periods or is shorter than the sum of the second and the third time periods.

It is clear that for the same altering function there can be numerous ways to define the start point and the end point of the first, the second and the third periods and consequently the lengths thereof. Particularly it is possible to define the time for the transition from the first to the second period and from the second to the third period in a number of ways for the same altering function. All the above cited ways have in common that the said three time periods fall within a definition in conformity with which the average variation of the first liquid characteristic is higher in the first period, is smaller in the second period, and is in between during the third period.

According to an embodiment of the invention, the third time period is longer than the second time period or is longer than the sum of the first and the second time periods.

According to the invention, during an extracorporeal blood treatment at least one physical or chemical characteristic of a first liquid flowing towards a portion of an extracorporeal blood treatment apparatus is altered in accordance with an altering function, at least one physical or chemical characteristic of a second liquid flowing from said apparatus portion changing in response to said alteration of said first liquid characteristic, at least one value of said second liquid characteristic being measured and used for computing at least one patient or treatment or apparatus parameter, the altering function comprising at least: a first time period in which the first liquid characteristic varies in one direction, regarded as positive, from an initial set value to a maximum set value; after the first time period, a further time period in which the first liquid characteristic decreases directing towards or reaching an essentially flat curve at a constant set value greater than the initial set value.

According to an embodiment of the invention, the first time period is at least twice as short as the further time period.

According to an embodiment of the invention, the first initial set value is a prescribed treatment value.

According to an embodiment of the invention, the first liquid characteristic reaches an end set value, which is a prescribed treatment value.

According to an embodiment of the invention, the first liquid characteristic could be the conductivity, or at least one ion concentration, or the temperature, or the density, or the viscosity, or an optical parameter like absorbance (or transmittance) or color, or any parameter reflecting the first liquid composition.

According to an embodiment of the invention, the second liquid characteristic could be the conductivity, or at least one ion concentration, or the temperature, or the density, or the viscosity, or an optical parameter like absorbance (or transmittance) or color, or any parameter reflecting the first liquid composition.

According to an embodiment of the invention, the altering function is determined as a function of a flow rate of the first liquid.

According to an embodiment of the invention, the alteration of the first liquid characteristic is controlled on the basis of control signals correlated to measured values of the first liquid characteristic or to measured values of the second liquid characteristic or to measured values of both said liquid characteristics.

Further characteristics and advantages will be clearer from the detailed description of a preferred though not exclusive embodiment of an apparatus for determining parameters during an extracorporeal blood treatment, of an extracorporeal blood treatment apparatus comprising said determining apparatus and of a method for operating said treatment apparatus for determining patient or treatment parameters during the treatment, according to the present invention.

BRIEF DESCRIPTION OF THE DRAWINGS

This description will be given below with reference to the appended drawings, which are provided as a mere guidance and are therefore not limiting, in which:

FIG. 1 shows a diagram of an extracorporeal blood treatment apparatus according to the present invention;

FIG. 2 shows a diagram describing the dynamics of a clean dialysate ultrafilter;

FIG. 3 shows the diagram of FIG. 2 wherein a dynamic compensation of the set point upstream the clean dialysate ultrafilter is introduced according to the present invention;

DETAILED DESCRIPTION

Figure 4:
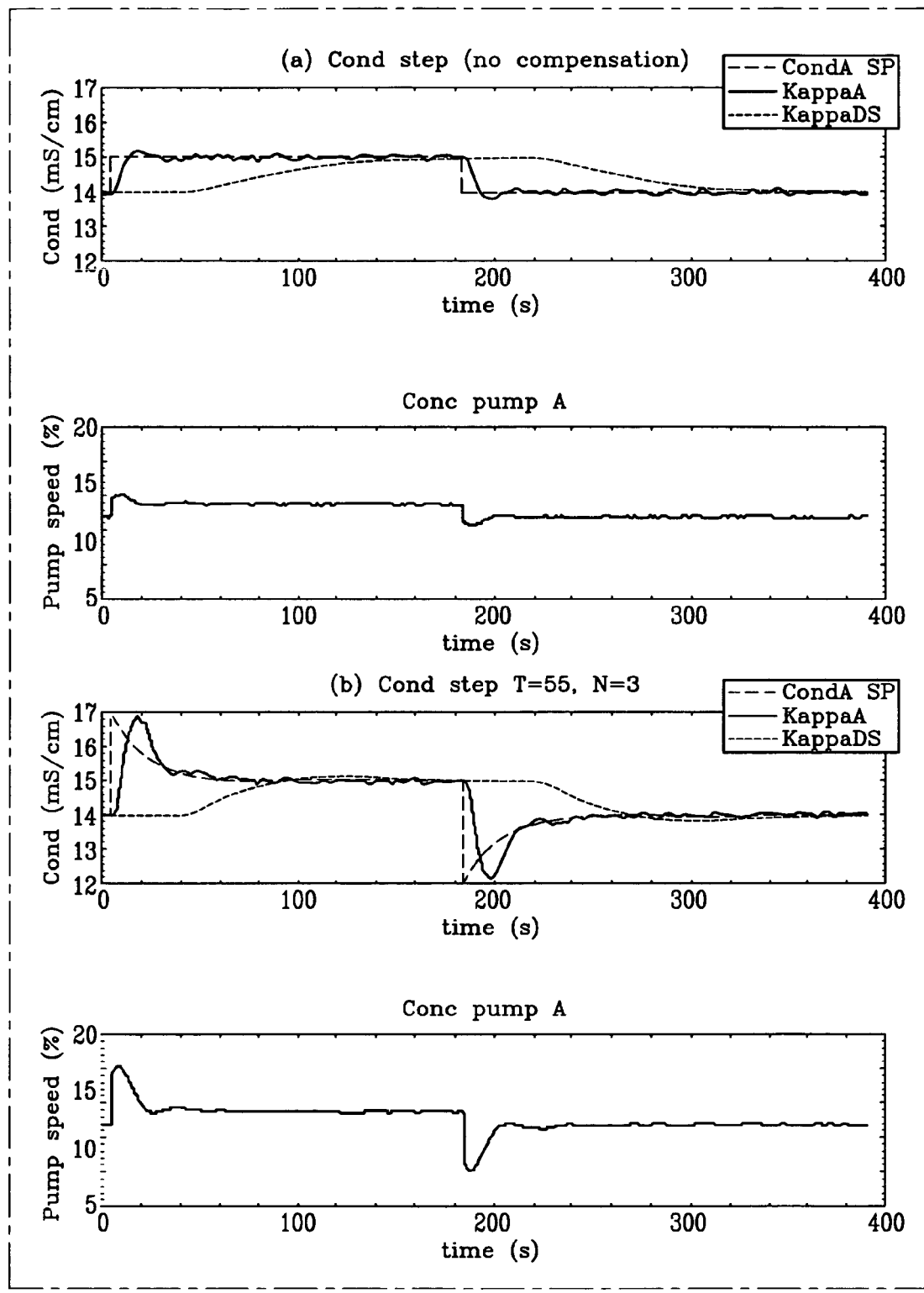
FIGS. 4 to 7 show diagrams of test results at different flow rates, describing how the settling time of the response after a clean dialysate ultrafilter to a conductivity step is reduced by using the present invention.

In this specific embodiment the extracorporeal blood treatment apparatus illustrated in FIG. 1 is a dialysis apparatus 1 (in more detail an apparatus for hemodiafiltration having an on-line preparation system for the preparation of the dialysis fluid) comprising a dialysate circulation system 2 that in use is connected to a dialysate chamber of a dialyzer 3.

The dialyzer 3 has a semipermeable membrane 4 that separates the dialysate chamber 5 from a blood chamber 6.

In use the blood chamber 6 is connected to a patient by a blood circulation system 7 in which a blood pump 8 conducts the blood into the blood chamber 6 through an arterial line 9 that is fluidly connected to a patient vascular access, and the treated blood is returned to the patient through a venous line 10.

The dialysate circulation system 2 comprises a dialysate preparation system 11 comprising in turn a dialysate preparation line 12 having a depurated water inlet 13 and three injection devices for injecting substances into the dialysate preparation line at three injection points 14, 15 and 16.

Each injection device comprises an injection line 17, 18 and 19 having a depurated water inlet 20, 21 and 22, a concentrated solution 23, 24 and 25 arranged on the injection line and through which the depurated water passes for generating a flow of a desired solution, and an injection pump 26, 27 and 28 for circulating and dosing the flow of the desired solution.

In this specific embodiment the three concentrated solutions are a bicarbonate solution 23, a several ions solution 24 and a sodium solution 25.

The dialysis apparatus 1 comprises a depurated water preparation system 29 comprising in turn: a water inlet 30 and a water filter 31 having an inlet 32 connected to the water inlet 30, a waste water outlet 33 connected to a drain and a depurated water outlet 34. The depurated water outlet 34 of the water filter is connected to the depurated water inlets 20, 21; 22 and 13 of the injection devices and, respectively, of the dialysate preparation line through a hydraulic distribution circuitry 35, of a known type, which is only diagrammatically illustrated as a block.

Three conductivity measurement devices 36, 37 and 38 are arranged after each injection point 14, 15 and 16 to measure the conductivity of the dialysate and to emit corresponding signals used for controlling the injection devices.

More in detail, each of the conductivity measurement devices 36, 37 and 38 emits a signal of measured conductivity, which is used by the control and calculation unit 52 to compute a command signal for the corresponding pump.

The dialysate circulation system comprises a dialysate supply line 39 which is the continuation of the dialysate preparation line 12 and which is connected to an inlet 40 of the dialysate chamber 5 of the dialyzer 3.

A dialysate supply pump 41 is arranged on the dialysate supply line 39 to circulate the fresh dialysate in a predetermined direction 42.

A clean dialysate filter 43 is arranged on the dialysate supply line 39 upstream the dialyzer 3. The clean dialysate filter has a dialysate inlet 44 and a clean dialysate outlet 45 which are connected to the dialysate supply line 39. The clean dialysate filter 43 further has a waste outlet 46 connected to a drain.

In this specific embodiment a conductivity measurement device 47 is arranged on the dialysate supply line 39 to measure the conductivity of the clean dialysate after the clean dialysate filter 43 and before the dialyzer 3 and to emit a corresponding signal. This signal may be (but normally is not) used for controlling one or more of the injection devices.

The dialysate circulation system comprises a dialysate waste line 48 that is connected to an outlet 49 of the dialysate chamber 5 of the dialyzer.

A waste dialysate pump 50 operates on the dialysate waste line to circulate the waste dialysate towards a drain.

In this specific embodiment a conductivity measurement device 51 is arranged on the dialysate waste line 48 to measure the conductivity of the waste dialysate and to emit a corresponding signal. This signal may be (but normally is not) used for controlling one or more of the injection devices.

Each conductivity measurement device 36, 37, 38, 47 and 51 generates a signal.

A control and calculation unit 52 is predisposed to receive the signals generated by the conductivity measurement devices 36, 37, 38, 47 and 51 and to operate the injecting devices, in particular the injection pumps 26, 27 and 28, based on the said signals. Normally only one conductivity signal is used to control each injection device, although it is possible to let the control loops affect each other, or to have two control loops working in a cascade, so that one conductivity signal is used in an inner loop to affect the injection device directly, and another conductivity signal in an outer loop is used to control the set point of the inner loop.

Herein below some operative methods are defined by means of which a processor in the control and calculation unit 52 of the apparatus can monitor the treatment.

An operative method according to the invention operates an extracorporeal blood treatment apparatus for determining treatment and/or patient and/or apparatus parameters during an extracorporeal blood treatment.

During the treatment at least one first liquid is circulated towards an inlet of at least one portion of the blood treatment apparatus.

The first liquid can be both a treatment liquid (for example fresh dialysate) and a corporal liquid (for example blood to be treated). In the embodiments of this detailed description the first liquid is a treatment liquid.

The portion can include one or more volumes of the flow system of the blood treatment apparatus such as, for example, one or more filter units.

The filter unit can be, for example, a filter for a treatment liquid, such as a clean dialysate filter, or a filter for a treatment of a corporal liquid, such as a dialyzer.

During the treatment at least a second liquid flows from an outlet of the portion of the blood treatment apparatus.

The second liquid can be both a treatment liquid (for example spent dialysate) and a corporal liquid (for example treated blood). In the embodiments herein described in detail the second liquid is fluidly connected to the same chamber of the filter unit to which the first liquid is fluidly connected. However, in other embodiments the second liquid can be separated from the chamber of the filter unit to which the first liquid is fluidly connected. In other words, in some embodiments the flow of the second liquid after the filter unit is the fluidic prosecution of the flow of the first liquid before the filter unit, but in other embodiments the flow of the second liquid flow is separated from the flow of the first liquid.

The method for operating the apparatus comprises a stage of altering a physical or chemical characteristic of the first liquid during its circulation towards the portion of the treatment apparatus.

In the specific embodiment the above characteristic is the conductivity, but other characteristic can be selected such as, for example, the temperature, or the concentration of an indicator solution, or the concentration of at least one ion, or the density, or the viscosity, or an optical parameter like absorbance (or transmittance) or color, or any parameter reflecting the first liquid composition.

The conductivity is altered by injecting at least one ionic substance into the flow of the first liquid by means of one or more of the three injection devices.

The method comprises a stage of measuring a change of a physical or chemical characteristic of the second liquid during its flow from the apparatus portion, in which the aforementioned change is in response to the alteration of the physical or chemical characteristic of the first liquid.

In this specific embodiment the physical or chemical characteristic of the second liquid is the same physical or chemical characteristic of the first liquid.

The first liquid can be a fresh dialysis liquid before the clean dialysate filter. The first liquid flows towards the cleaning filter (clean dialysate filter) for a treatment liquid (dialysate), the cleaning filter being arranged upstream of a blood treatment unit (dialyser).

The second liquid can be the spent dialysis liquid after the dialyzer. The second liquid can also be the fresh dialysis liquid after the clean dialysate filter and before the dialyzer.

The method comprises a stage of computing at least one significant parameter based on the driven alteration of the first liquid characteristic and the responsive change of the second liquid characteristic.

The significant parameters to be determined can be, for example, ionic dialysance or clearance, plasma conductivity, plasma sodium concentration, dialysis dose, depurated volume of patient body water, ionic mass balance, blood recirculation, fistula flow, etc.

The computing stage is essentially of known type and therefore it will not be described in further detail.

According to the invention, the altering stage is performed on the basis of the following theoretical considerations.

Theoretical Considerations—Discrete Time.

We assume that the first liquid is the fresh dialysis liquid before the clean dialysate filter (ultrafilter) and the second liquid is the cleaned fresh dialysis liquid after the clean dialysate filter and before the dialyzer.

We also assume that the first liquid characteristic is the conductivity and that also the second liquid characteristic is the conductivity.

The conductivity of the first liquid is controlled at sample intervals by adjusting the speed of at least one concentrate pump until the conductivity in at least one measurement device agree with at least one set value or a set curve.

We assume to profile a curve of the set alteration of the conductivity of the first liquid as a function of time and we denote this curve by u(t).

We denote the curve of the actual alteration of the conductivity of the second liquid as a function of time by c(t). In other words, c(t) represents the actual conductivity response to a set change of the conductivity.

If we assume that the conductivity response to a set conductivity change is like a first order filter in discrete time with a unit sample interval and a unit gain, we have $$c(t+1) = a \cdot c(t) + (1-a) \cdot u(t) \quad (1)$$

The constant a characterizes the speed of the clean dialysate filter.

In these considerations we will use a mathematical model of discrete time type. It is known that the case with discrete time is usually realized using computers. In discrete time the transform usually used is the z-transform, where z, which is the argument of the discrete time transfer function, is the shift operator. It is known that a multiplication by z implies a shift in time one sampling step forward, and a multiplication by $z^{-1}$ implies a shift in time one sampling step backward.

It is here assumed that, for the discrete time case, the time constant of a function is determined by the coefficient for $z^{-1}$ in the denominator of the function.

Using the discrete z-transform with C(z) and U(z) denoting the transforms of c(t) and u(t), (1) can be written:

$$C(z) = \frac{(1-a)}{z-a} U(z) = G(z)U(z) \quad (2)$$

G(z) is the discrete time transfer function that describes how c(t) changes in response to changes in u(t). In equation (2) this filter is of first order. This was chosen to simplify the discussion, but any type of transfer function G(z) could be assumed.

The time constant is defined as 1/(1−a) sample intervals. This assumption is based on the following considerations.

We assume to define the time constant of a discrete time system as the time constant of the corresponding continuous time system (which is the coefficient for s in the denominator of a first order system, or equivalently 1/b if s+b is the denominator). When such a continuous time system is sampled with the sample period h, the coefficient "a" in the equation (2) will be $e^{-bh}$, which for small h is approximately 1−bh. This means that the time constant 1/b will be roughly equal to h/(1−a), i.e. 1/(1−a) sample intervals. So this could be said to be a definition of the discrete time constant.

As a general approach u(t) can now be chosen as a filtered version of a desired conductivity response w(t).

In terms of the z-transforms, U(z) is chosen as $$U(z) = H(z)W(z) \quad (3)$$

where W(z) is the z-transform of the desired conductivity response and H(z) is the discrete transfer function to be chosen to get the desired response.

Inserting (3) into (2) we get $$C(z)=G(z)H(z)W(z) \quad (4)$$

From (4) we see that if we choose H(z)=1/G(z) we will have C(z)=W(z), and therefore c(t)=w(t) as desired.

We should therefore have $$H(z) = \frac{z-a}{1-a} \quad (5)$$

which means that $$u(t) = \frac{w(t+1) - a \cdot w(t)}{1-a} \quad (6)$$

We would then have to know w in advance, since w(t+1) is present on the right hand side and is needed at time t to calculate u(t). Therefore it is reasonable to accept that the response is delayed one step so that we only get $$c(t)=w(t-1) \quad (7)$$

This corresponds to the introduction of an extra factor z in the denominator of H(z).

In equation (6) (or equivalently in equation (5)) if the conductivity response is slow, the parameter a will be close to one, maybe 0.95-0.99. This means that the coefficients in (6) will be large, and a large compensating effect is needed in order to cancel out completely the filtering effect. This would require large temporary set points, which would result in saturation in the control loop for conductivity.

A remedy to this problem is to accept that the final response to a desired conductivity change is not immediate. Instead the original slow response is replaced by a much quicker response, but one which is still described by a time constant. This is done by including this new time constant in the filter H(z). A possible choice in the first order situation described by (2) is $$H(z) = \frac{z-a}{1-a} \cdot \frac{1-\alpha}{z-\alpha} \quad (8)$$

We can rewrite (8) as $$H(z) = \frac{z-a}{1-a} \cdot J(z) = \frac{J(z)}{G(z)} \text{ where } J(z) = \frac{1-\alpha}{z-\alpha}$$

The new time constant that is introduced is approximately $1/(1-\alpha)$ sample intervals, which should be made considerably shorter than the old time constant $1/(1-a)$, for example 2 to 5 times shorter. When (8) is introduced into (2) and (3) we see that $$C(z) = \frac{(1-a)}{z-a} H(z) W(z) \quad (9)$$

$$= \frac{(1-a)}{z-a} \frac{z-a}{1-a} \cdot \frac{1-\alpha}{z-\alpha} W(z)$$

$$= \frac{1-\alpha}{z-\alpha} W(z) = J(z)W(z)$$

Provided that our knowledge about the conductivity response is perfect, so that the correct value for the constant a can be used in (8), we can thus replace the time constant with the new one. If the mismatch is not too large between the value for a that is assumed in (8), and the true value, we will still get approximately the same result.

Let us now look at the size of the parameters in (8), and compare to (6). We can then rewrite (8) as $$H(z) = \frac{z-a}{1-a} \cdot \frac{1-\alpha}{z-\alpha} \quad (10)$$

$$= \frac{1-\alpha}{1-a} \cdot \left(1 - \frac{a-\alpha}{z-\alpha}\right)$$

$$= \frac{1-\alpha}{1-a} - \frac{a-\alpha}{1-a} \cdot \frac{1-\alpha}{z-\alpha}$$

The first term on the bottom side $(1-\alpha)/(1-a)$ is a constant, which is larger than 1 if the new time constant is shorter than the old one ($\alpha<a$).

The second term on the bottom side is the new first order filter with a scaling factor $(a-\alpha)/(1-a)$.

If we assume that a=0.98 and α=0.94, which corresponds to making the system 3 times faster, we see that the first constant is 3 and the scaling factor is 2. These are much more reasonable constants than the 50 that would be the result of using (6).

For a desired set increment step of 1 mS/cm this would imply an immediate change in conductivity set point of 3 mS/cm instead of 1 mS/cm, and the set point would then be gradually decreased to 1 mS/cm at a speed determined by the new time constant $1/(1-\alpha)$=16.7 sample intervals.

The set alteration curve of the first liquid characteristic before the filter is changed, with respect to a simple alteration made by a step, in a way that will make the second liquid characteristic after the filter change more quickly, i.e. to look more like a step.

This can be done by using an inverse filter on the set alteration curve of the first liquid characteristic.

In principle, this inverse filter can be calculated as the inverse of a filter that describes how the second liquid characteristic changes in response to a change in the first liquid characteristic set point.

The principle above is not limited to first order conductivity responses G(z). Any type of responses can be handled by including in the filter H(z) both components that are aimed at canceling out the whole or parts of G(z), and components that are aimed at introducing new, faster dynamics.

The compensation is dependent on the filter used, so different H(z) are derived for different filters, and knowledge of which filter is used can be available in the machine. The apparatus can thus be provided with means for identifying the filter or filters, including ultrafilters, dialyzers and all types of filters or other volumes of the flow system that can be operatively associated to the apparatus.

The conductivity response could be referred to the conductivity after the dialyzer, or whatever filter used in the extracorporeal blood treatment apparatus, instead of the conductivity after the ultrafilter. The aim would then be to make the conductivity after the dialyzer, or other filter, change and assume a new steady state as quickly as possible. This possibility is considered as part of the invention.

Theoretical Considerations—Continuous Time.

It is assumed that a dynamic first order compensation of the set alteration is used to speed up the conductivity response in the HDF/HF apparatus of FIG. 1 which has a clean dialysate filter (ultrafilter).

We consider that the first liquid is the fresh dialysis liquid before the clean dialysate filter and the second liquid is the cleaned fresh dialysis liquid after the clean dialysate filter and before the dialyzer.

It is also assumed that the dynamics from a change in the conductivity set values before the clean dialysate filter (ultrafilter) to the conductivity values measured at the dialyzer inlet, i.e. after the clean dialysate filter, can be modeled as a transport time delay $T_d$ and a first order low pass filter with a time constant T. The transfer function of such a system is $$G(s) = G_f(s) \cdot G_d(s) = \frac{1}{1+s \cdot T} \cdot e^{-sT_d}$$

In this case the mathematical model of the filter dynamics is a continuous time model and the transfer function is a Laplace transform, or equivalently an operator which is a function of the derivation operator s. This example is done since the invention may be carried out using analog electronics, which by nature is continuous time.

This dynamic process model is diagrammatically illustrated in FIG. 2.

This model is of course only a crude first approximation.

The mixing dynamics of the ultrafilter will provide the dominating time constant in the system. There will also be other time constants that contribute to the shape of the step response, originating e.g. from the dynamics of the conductivity feedback control system and additional mixing volumes such as bubble traps etc.

For the time being, it is assumed that these additional dynamics can be neglected.

If we model the ultrafilter as a perfectly stirred mixing tank, the time constant T has the value $$T = V/q$$

where V is the ultrafilter volume and q is the fluid flow through the ultrafilter.

It is assumed, as an example, that the ultrafilter has a priming volume of 163 ml (lumen) plus 295 ml (filtrate side), i.e. a total fluid volume of 458 ml. Since there is no flush of the ultrafilter during treatment, the fluid flow must pass through both these volumes. We may thus assume that the total filter volume should be used in the calculation of the filter time constant.

With V=458 ml and q=500 ml/min, we get a time constant T=0.916 min=55 sec, i.e. just below one minute.

In order to speed up the sluggish conductivity step response after the ultrafilter, we used the dynamic compensation concept of the present invention.

The basic idea is to change the conductivity set point before the ultrafilter in a way that will make the conductivity after the ultrafilter change more quickly, i.e. to look more like a step.

Let $G_c(s)$ denote the transfer function of the compensation function, which is used to calculate a compensated set value for the conductivity control loop.

We then get the system diagrammatically illustrated in FIG. 3.

In principle, we would like to select $G_c(s)$ such that the overall transfer function from conductivity set values to measured conductivity values after the ultrafilter is unity, so that we have a perfect step response.

Now, in order to compensate for the transport time delay in the system, we would need to know future set values. This is not necessary in practice, however, since we can eliminate the delay by a time shift of the measured values in the calculations. What remains then, is to compensate for the filter time constant of the system.

Let us select $G_c(s)$ such that $$G_c(s) \cdot G_f(s) = G_c(s) \cdot \frac{1}{1+sT} = 1 \Leftrightarrow G_c(s) = \frac{1}{G_f(s)} = 1+sT$$

The perfect compensation function is calculated as the inverse of the filter transfer function that describes how the conductivity after the ultrafilter changes in response to a change in the conductivity set point before the ultrafilter.

This type of compensation function is not good for practical use.

The Laplace operator "s" corresponds to taking the derivative of the input signal, which is an operation that is very sensitive to noise.

We can accept the fact that the conductivity step response after the filter cannot follow the set change before the filter perfectly, so it will still be characterised by a time constant.

We can design a compensation that makes this time constant significantly smaller than the time constant of the uncompensated system.

We have assumed that the overall compensated system has a time constant T/N, i.e. that we wish to reduce the time constant (and the rise time) of the system with a factor N. We must then select $G_c(s)$ such that $$G_c(s) \cdot G_f(s) = G_c(s) \cdot \frac{1}{1+sT} = \frac{1}{1+s \cdot \frac{T}{N}} \Leftrightarrow G_c(s) = \frac{1+sT}{1+s\frac{T}{N}}$$

The "s" in the numerator still represents a derivative operation, but we now have a transfer function with the same polynomial degree in both the numerator and the denominator.

It is then possible to rewrite the compensation function so that it has a structure better suited for implementation without any derivative operations:

$$G_c(s) = \frac{1+sT}{1+s\frac{T}{N}} = N \cdot \left(1 - \frac{(1-1/N)}{1+s \cdot \frac{T}{N}}\right)$$

The compensation function will thus be the sum of a direct term with a gain N, and the output from a low pass filter with gain (N−1)/N and a time constant equal to the desired time constant of the overall system transfer function, T/N.

If the input signal to the compensation function is a step with amplitude A, the initial output will be a step with amplitude NA.

The output then converges towards the steady state level A with the time constant T/N.

As seen, this continuous time transfer function can be implemented in discrete time e.g. by a suitable difference approximation of the Laplace (derivative) operator s in the low pass filter.

As long as the sampling interval is short when compared to the filter time constant T/N, the discretization method will not be a critical design parameter.

EXAMPLES

In these examples a dynamic first order compensation of the set alteration has been used to speed up the conductivity response in the HDF/HF apparatus of FIG. 1 which has a clean dialysate filter (ultrafilter).

The first liquid was the fresh dialysis liquid before the clean dialysate filter and the second liquid was the cleaned fresh dialysis liquid after the clean dialysate filter and before the dialyzer.

A test was performed on the apparatus of FIG. 1 based on the following system parameter settings:

| | |
|---|---|
| Degassing pressure: | 100 mmHg (abs) |
| Dialysate main flow: | 300/500/900 ml/min |
| $T_{cA}$ dialysate temperature set value: | 37° C. |

Conductivity set value at measurement device 36 3.1 mS/cm [after $HCO_3$ infusion point 14]=34 mmol/l Conductivity set value at measurement device 37 3.1 mS/cm (concentrated solution 24 not used)

Conductivity set value at measurement device 38 14 mS/cm [after Na infusion point 16]=approx. 140 mmol/l Conductivity Step amplitude 1 mS/cm In practice, the initial set value=14 mS/cm and the set value after the step=15 mS/cm.

The control and calculation unit 52 comprises a PID controller which uses the conductivity feedback signal measured by the conductivity measurement device 38 and which controls the concentration pump 28 under the following conductivity control parameters.

Sampling interval: 0.5 sec.

Proportional gain: K=1.5%/mS/cm at 500 ml/min; (1% pump speed≈1 ml/min concentrate flow); the conductivity control algorithm has a gain scheduling function where the proportional gain is proportional to the main flow $Q_o$.

Integral time: Ti=10 sec at 500 ml/min; the conductivity control algorithm has a gain scheduling function where the integral time is inversely proportional to the square root of the main flow $Q_o$.

Derivative time: Td=0 sec; D action not used.

The conductivity is controlled by adjusting the speed of the concentrate pump 28 until the conductivity in the measurement device 38, which is placed fairly close to the point 16 where concentrate is added, agree with the set values.

The conductivity feedback signal generated by the conductivity measurement device 38 was filtered with a first order discrete time low pass filter (time constant=5 sec) to reduce conductivity fluctuations caused by the pulsating flow from the concentrate pumps.

A forward difference approximation of the derivative operator in the set compensation low pass filter was used.

The function was executed with a cycle time of 0.1 sec.

With the set compensation described above, we would theoretically expect a reduction of the conductivity response rise time measured after the clean dialysate filter with a factor N.

The test results for a few different cases are shown in FIGS. 4-7.

Each figure contains two cases (each of FIGS. 4, 6 and 7 has one case without compensation and the other one with compensation, FIG. 5 contains two compensated cases with the uncompensated case shown in FIG. 4); each case has two diagrams with the following content (from top to bottom):

i) A first curve (CondASP) is the conductivity set curve downstream to the injection point 16 and upstream the clean dialysate filter 43. A second curve (KappaA) is the conductivity actual curve measured by measurement device 38 before the filter 43 (the measured values are filtered with filter time constant 5 sec). A third curve (KappaDS) is the conductivity actual curve measured by measurement device 47 after the filter 43.

ii) Concentrate pump 28 speed (%), where 100% speed≈100 ml/min.

All conductivity values shown in the diagrams are temperature compensated to 37.5° C. using known methods.

First Case.

Figure 5:
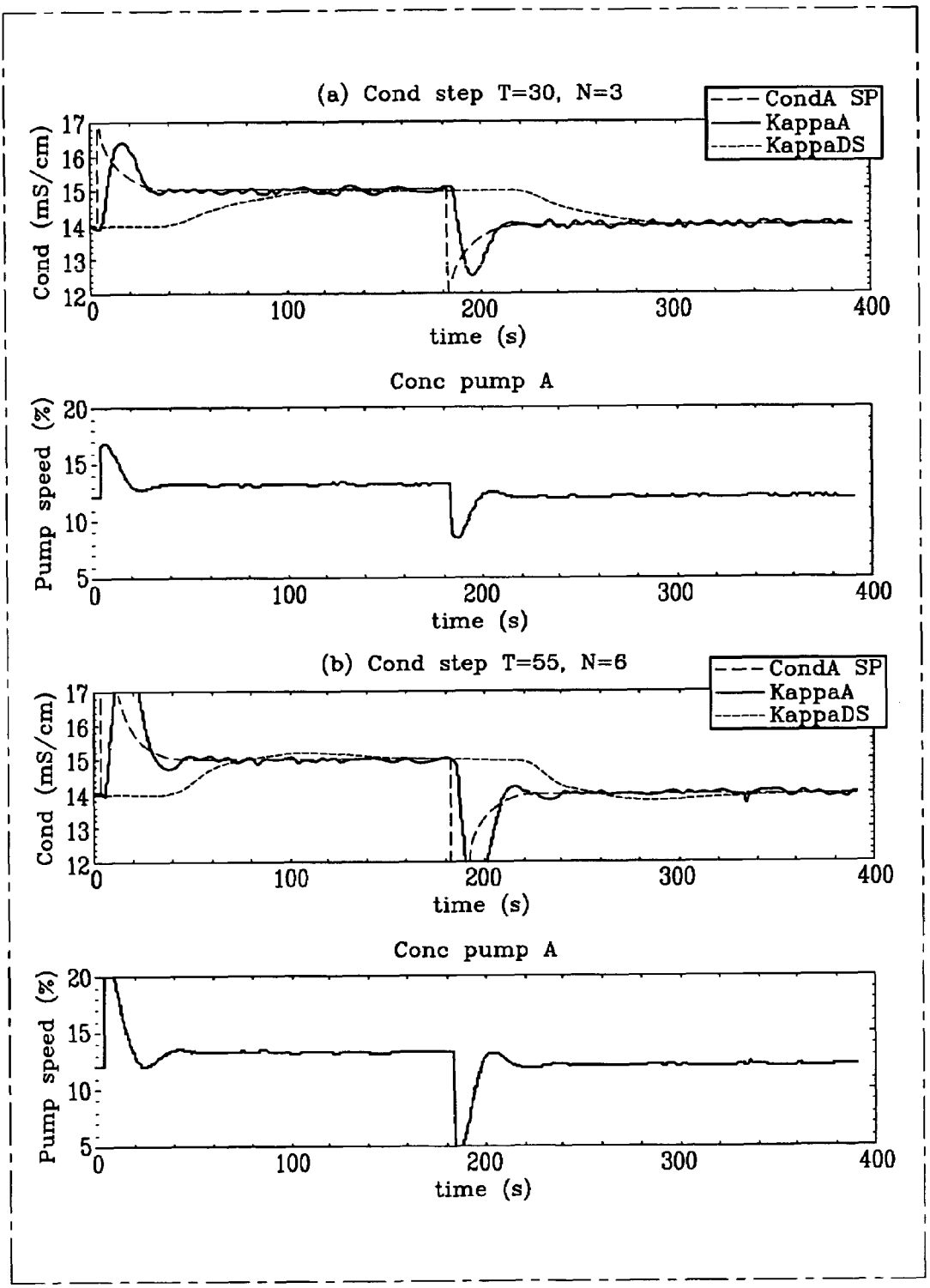

Nominal flow, $Q_o$=500 ml/min, FIGS. 4 and 5.

FIG. 4a shows the nominal conductivity step response at 500 ml/min main flow without any compensation of the set alteration curve.

The rise time is approximately $T_r$=90 sec. This is shorter than you would expect from the simple first order model of the ultrafilter dynamics, where the nominal time constant T=V/q=55 sec corresponds to a rise time $T_r$=2.2 T=120 sec.

With a set compensation using the nominal clean dialysate filter time constant T=55 sec and a speed-up factor N=3, you obtain the step response shown in FIG. 4b.

The value N=3 is chosen as a reasonable compromise between speed and transient conductivity set levels.

The response is significantly faster ($T_r$=40 sec) by using a compensation, but it also has a noticeable overshoot before reaching the steady state level.

This overshoot may create problems for the clearance calculations. The theoretical model does not predict this overshoot, and this suggests that the dynamic filter model assumptions are incorrect. One possible explanation to the overshoot is that the estimated filter time constant is too large. This hypothesis is also supported by the measured step response rise time without any compensation, which was shorter than expected.

If we keep N=3 and reduce the filter time constant to T=30 sec, we get the results shown in FIG. 5a. The step response now looks much better without any overshoot, but the rise time has increased a little ($T_r$=50 sec).

Finally, we also tested increasing the speed-up factor to N=6 in the nominal case (T=55 sec). The results are shown in FIG. 5b. The rise time is now much shorter ($T_r$=20 sec), but at the same time we get a very high initial set pulse (+6 mS/cm) that creates a large overshoot at the conductivity measurement device 38 and also an increased overshoot at the conductivity measurement device 47.

Second Case.

Low flow, $Q_o$=300 ml/min, FIGS. 6a and 6b.

FIG. 6a shows the nominal conductivity response at 300 ml/min main flow without any set values compensation.

The rise time is approximately $T_r$=150 sec. Again, this is shorter than you would expect from the simple first order model of the filter dynamics, where the nominal time constant T=V/q=92 sec corresponds to a rise time $T_r$=2.2 T=200 sec.

Also in this case, using a set compensation with the nominal filter time constant produces a step response with an overshoot.

With N=3, and a reduced time constant of T=60 sec we obtain the results shown in FIG. 6b. The rise time has decreased to $T_r$=83 sec, and there is only a very small overshoot.

Third Case.

High flow, $Q_o$=900 ml/min, FIGS. 7a and 7b.

FIG. 7a shows the nominal conductivity response at 900 ml/min main flow without any compensation. The rise time is approximately $T_r$=40 sec. This is also shorter than you would expect from the simple first order model of the ultrafilter dynamics, where the nominal time constant T=V/q=30 sec corresponds to a rise time $T_r$=2.2 T=66 sec.

With N=3, and a reduced time constant of T=20 sec we obtain the results shown in FIG. 7b. The rise time has decreased to $T_r$=20 sec, and there is only a very small overshoot.

It is interesting to note that at 900 ml/min main flow there is a noticeable offset of about 0.1 mS/cm between the conductivity measured at the device 38 and at the device 47. It is believed that this offset could be caused by a temperature measurement error in either (or both) of the conductivity measurement devices at high flow rates. This offset is a pure measurement-calibration problem, however, and it should not influence the analysis of our test results or the conclusions we can draw from them.

Summarizing:

FIG. 4: $Q_o$=500 ml/min

Case (a)=no compensation

Case (b)=compensation with T=55 and N=3.

Initial set value=14 mS/cm

Maximum set value=17 mS/cm

Step set value=15 mS/cm

Minimum set value=12 mS/cm.

For a desired increment (step) of conductivity value of 1 mS/cm at a steady state, we will have an immediate increment in conductivity set value of 3 mS/cm instead of 1 mS/cm, and the set curve will then be gradually decreased to 1 mS/cm at a speed determined by the time constant T.

FIG. 5: $Q_o$=500 ml/min

Case (a)=compensation with T=30 and N=3. If the time constant T is decreased then the set curve, after the initial immediate increment, will be decreased more quickly.

Case (b)=compensation with T=55 and N=6. In this case (N=6):

Initial set value=14 mS/cm

Maximum set value=20 mS/cm

Step set value=15 mS/cm

Minimum set value=9 mS/cm.

Figure 6:
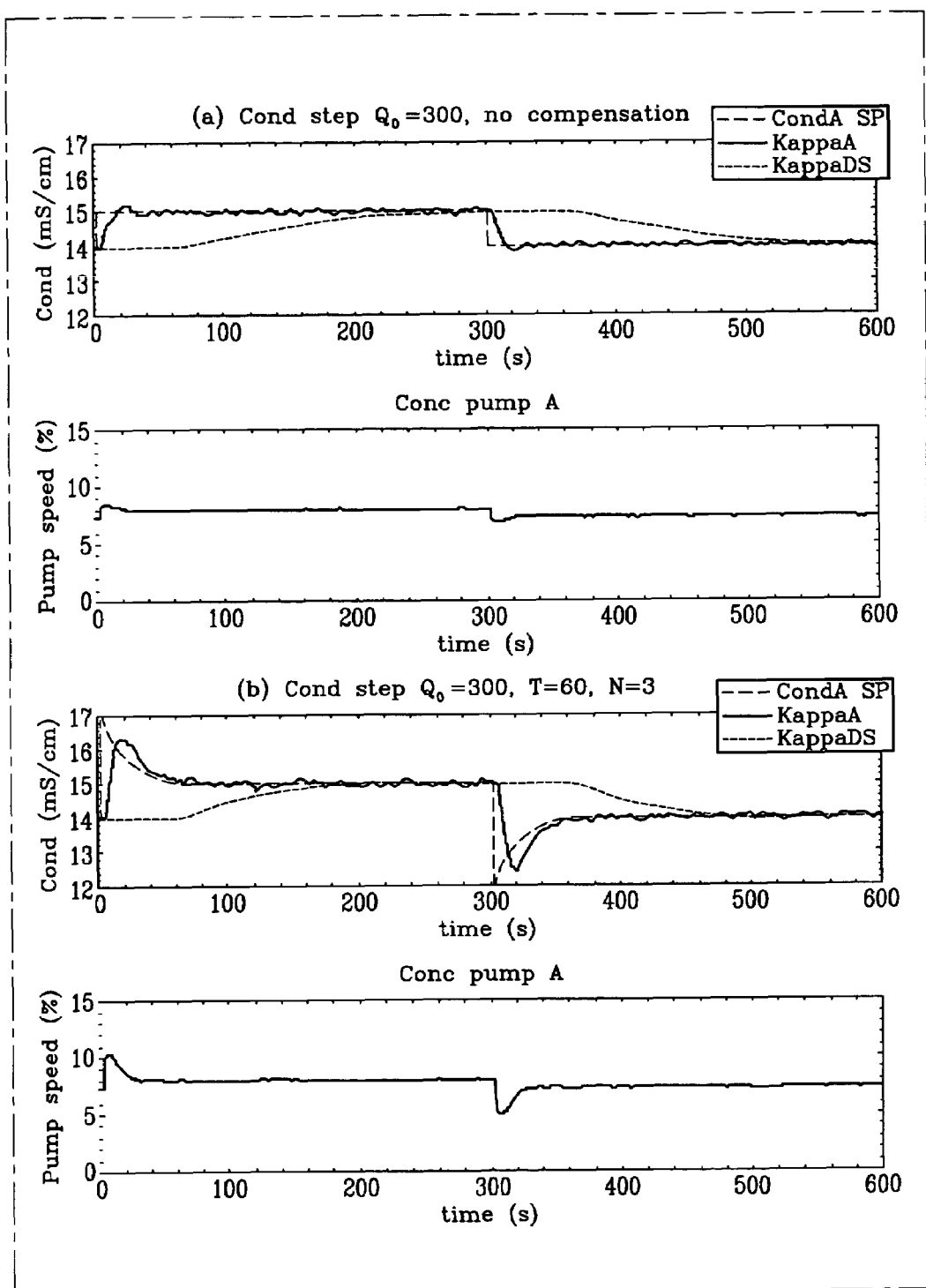

FIG. 6: $Q_o$=300 ml/min

Case (a)=no compensation

Case (b)=compensation with T=55 and N=3.

Figure 7:
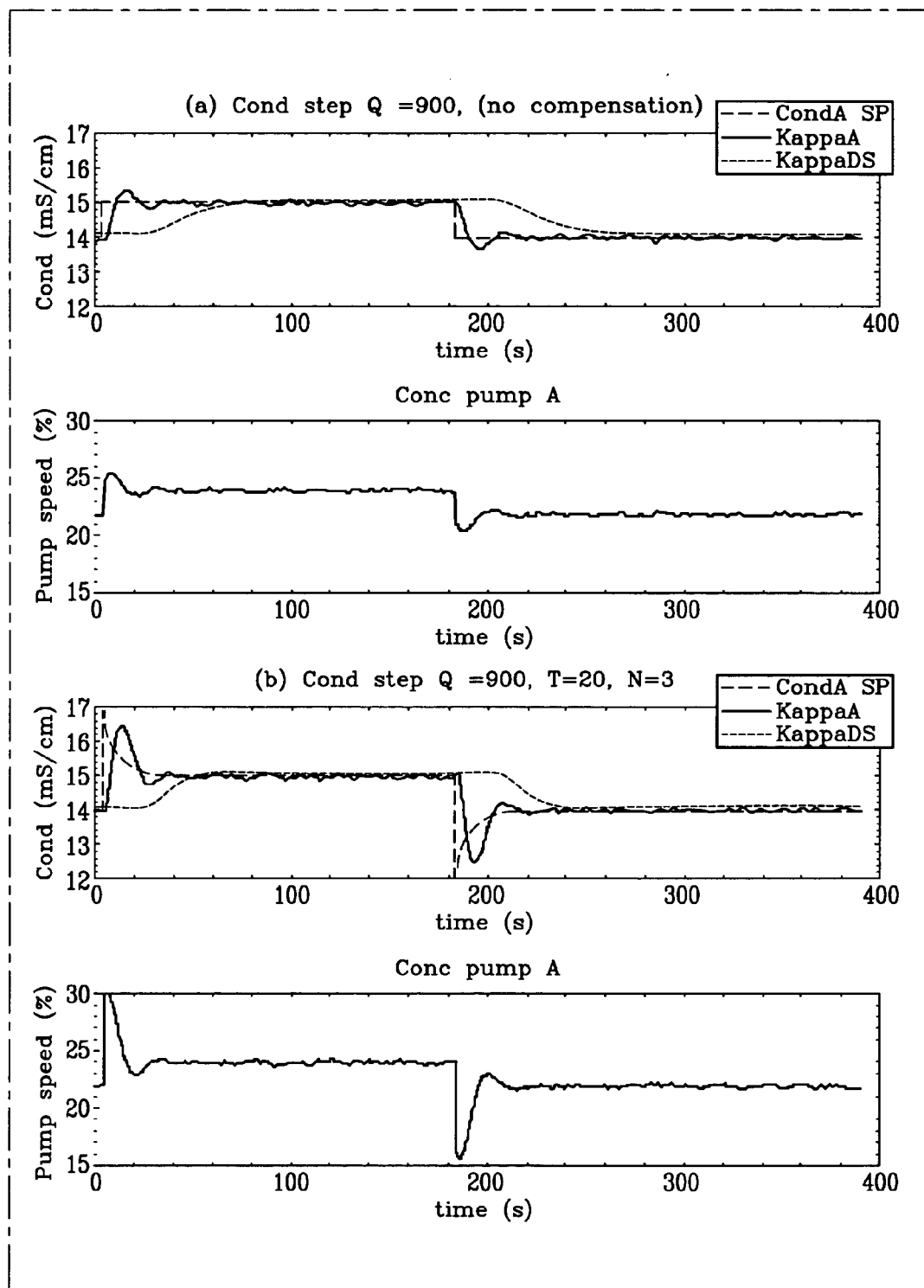

FIG. 7: $Q_o$=900 ml/min

Case (a)=no compensation

Case (b)=compensation with T=20 and N=3.

The numerical results of the investigation are summarized in table 1 below.

If we tune the compensation time constant to obtain a nicely shaped step response while maintaining an initial set alteration step which is not more than three times the desired alteration amplitude (i.e. N=3), it is possible to reduce the conductivity response rise time to approximately half of the uncompensated value.

TABLE 1

Conductivity response test results

| Test case (FIG.) | $Q_o$ ml/min | $T_f$ sec | $T_c$ sec | N | $T_r$ sec | Comment |
|---|---|---|---|---|---|---|
| 4a | 500 | 55 | 0 | 0 | 90 | Nominal case (500 ml/min) |
| 4b | 500 | 55 | 55 | 3 | 40 | Conductivity overshoot after the filter |
| 5a | 500 | 55 | 30 | 3 | 50 | Nicely shaped response, no overshoot |
| 5b | 500 | 55 | 55 | 6 | 20 | Large conductivity pulse before the filter (+6 mS/cm) and conductivity overshoot after the filter |
| 6a | 300 | 92 | 0 | 0 | 150 | Nominal case (300 ml/min) |
| 6b | 300 | 92 | 60 | 3 | 83 | Nicely shaped response, small overshoot |
| 7a | 900 | 30 | 0 | 0 | 40 | Nominal case (900 ml/min) |
| 7b | 900 | 30 | 20 | 3 | 20 | Nicely shaped response, small overshoot |

Notation:
N Compensation function speed-up factor
$Q_o$ Dialysis fluid flow rate
$T_f$ Nominal filter time constant, $T_f = V/Q_o$ where V is the total filter volume
$T_c$ Filter time constant used in compensation function
$T_r$ Response rise time (10-90%) measured after the filter The critical case in terms of total settling time of the system is minimum flow (300 ml/min), where the response of the compensated system still has a rise time of more then 80 sec. To this value we must then add the transport delay, which is more than 60 sec at 300 ml/min in the tested system.

In order to speed up the response further, we can increase the parameter N to higher values, but with the limitation that too high values can lead to too large conductivity transients at the conductivity measurement device before the filter.

Another way to speed up the response further is to use a model of the ultrafilter dynamics having an order higher than one.

These transients may be undesirable from a safety point of view and also considering the aspects of conductivity cell calibration range.

At high flow rates, there is a potential risk that the set alteration pulse needed to speed up the response will cause the concentrate pump to saturate, i.e. reach the maximum concentrate flow limit.

The above example shows that the settling time of the conductivity step response measured after a filter, in particular after a clean dialysate filter, in the fluid path can be reduced by introducing a dynamic compensation of the conductivity set values before the filter.

In particular the above example shows that, with a simple first order set value compensation function, it is possible to reduce the conductivity step response rise time to about half of the uncompensated value while still maintaining a nicely shaped step response without significant overshoot and an initial transient set value change which is not bigger than three times the desired step amplitude.

The present invention is not limited to a first order set value compensation function. Other types of compensation function can be used.

In these examples the physical or chemical characteristic response has been referred to the characteristic after the ultrafilter. In other embodiments it could be referred to the physical or chemical characteristic after the dialyzer or other kind of filter or other volumes used in a blood treatment apparatus.

In these cases the aim would be to make the characteristic after the dialyzer, or other filter or group of filters, or other volumes or group of volumes, change and assume a new steady state as quickly as possible.

As seen, the response to a first liquid characteristic alteration can depend on the flow rate of the first liquid. Thus the control and computer system 52 can be programmed for operating the altering device according to an altering function that is determined as a function of the flow rate of the first liquid.

In the above examples, the physical or chemical characteristic of the first liquid and of the second liquid is the conductivity.

In other embodiments, the above cited characteristic can be, for example, the concentration of an indicator solution injected into the first liquid in a injection point. The indicator solution can have acoustical properties different from those of the first liquid upstream the injection point. In this case the measuring device can be an ultrasound-measuring device which registers a change in the concentration of the indicator solution in the first liquid based on a change in the diffusion rate of ultrasound.

In further embodiments, other characteristics can be used such as, for example, temperature, or density, or the viscosity, or an optical parameter like absorbance (or transmittance) or color, or any parameter reflecting the first liquid composition.

Figure 8:
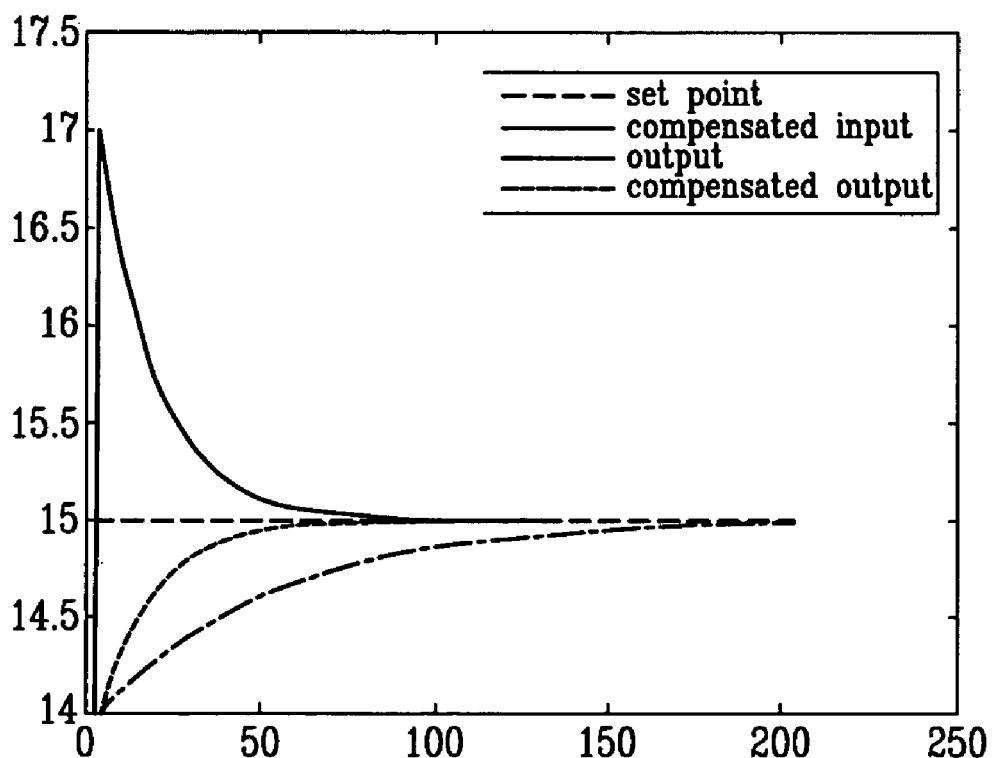
FIGS. 8 to 10 show diagrams of dynamic compensation of three different inputs of the conductivity set point.
Figure 9:
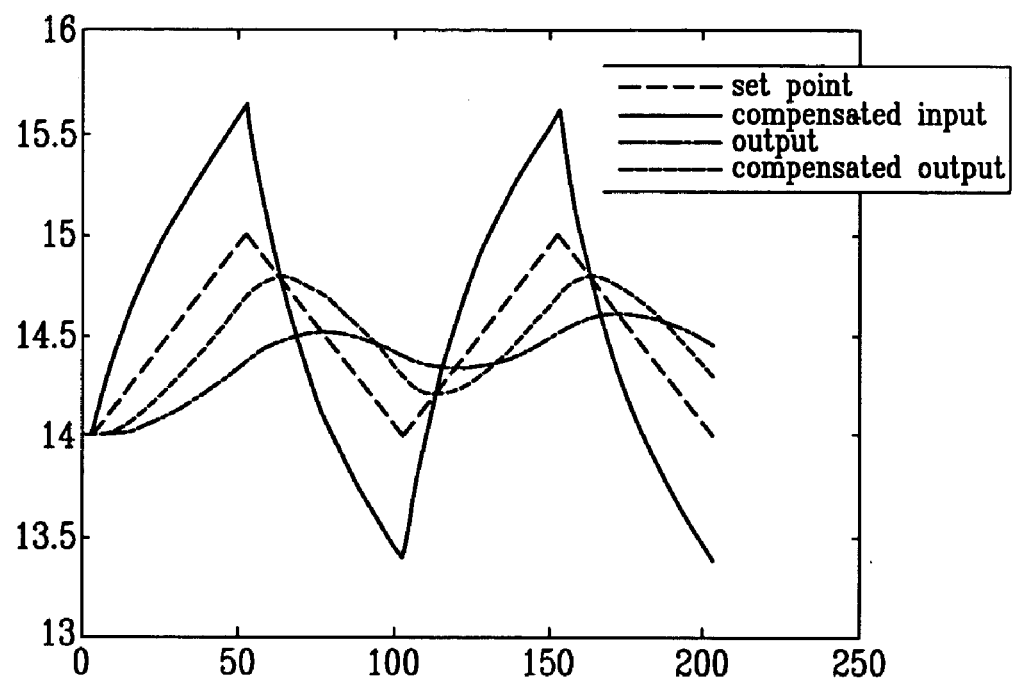
Figure 10:
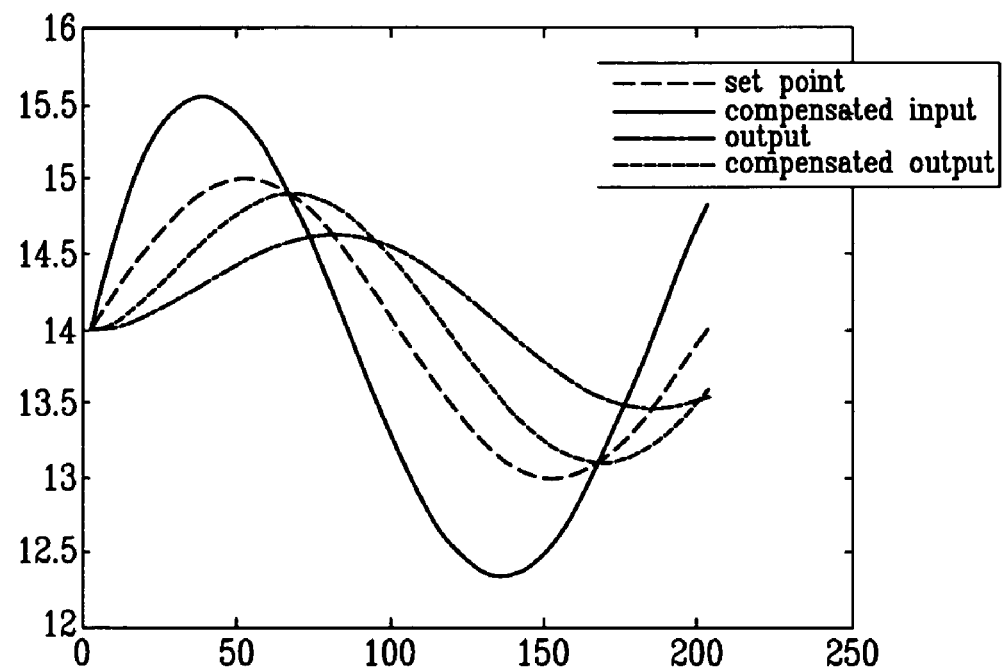

Finally, FIGS. 8 to 10 show three different cases with three different set point inputs of the first liquid characteristic and the corresponding outputs of the second liquid.

Each case comprises four curves:
set point=uncompensated alteration of the first liquid=the desired set point,
compensated input=compensated alteration of the first liquid=the compensated input that is needed to create the compensated output,
output=change foreseen for the second liquid in response to the set point=the output that is generated by the desired set point directly,
compensated output=change foreseen for the second liquid in response to the compensated input=the compensated output resulting from using the compensated input.

A computer program generated these curves.

For these simulations it was used a first order system sampled once per second with a time constant of 50 samples (seconds). This means a system filter constant of 0.98. The desired response should be 3 times faster, which means a filter constant of 0.94.

FIG. 8 shows a first case in which the desired set point of the first liquid characteristic alteration consists in a step.

FIG. 9 shows a second case in which the desired set point of the first liquid characteristic alteration is triangle shaped with a ramp and a slope.

FIG. 10 shows a third case in which the desired set point of the first liquid characteristic alteration has a sinusoidal shape.

Many other types of desired input can be selected as, for example, a square shaped input, or a sawtooth shaped input, or a rectangular shaped input, etc.

In the aforementioned examples the altering stage comprises a first time period in which the first liquid characteristic varies with an average variation over time having a first value different from zero and regarded as positive.

The altering stage comprises, after the first time period, a second time period in which an average variation over time of the first liquid characteristic has a second value smaller than the first value, wherein "smaller" means that a comparison is done considering not only the absolute values of the variations over time but also whether they are positive or negative.

The altering stage also comprises, after the second time period, a third time period in which an average variation over time of the first liquid characteristic has a third value smaller than the first value and greater than the second value, wherein "smaller" and "greater" means that comparisons are done considering not only the absolute values of the variations over time but also whether they are positive or negative.

In other words, the altering stage has a first phase in which the first liquid characteristic increases (or decreases) relatively quickly on average, a second phase in which the increase (or decrease) is slower on average than in the previous first phase, and a third phase in which the increase (or decrease) is faster on average than in the previous second phase but slower than in the previous first phase. Considering for example the curve of FIG. 8 describing the compensated set point of the first liquid characteristic, the curve has a first phase in which the first liquid characteristic increases relatively quickly from 14 to 17 mS/cm, a second phase in which the increase is slower (the first liquid characteristic actually gradually decreases from 17 towards 15 mS/cm, such a decreasing course being considered as a negative increase and thus slower than in the first phase), and a third phase in which the first liquid characteristic is more or less constant at 15 mS/cm, such a flat trend being considered as a zero increase and thus greater than the negative increase of the second phase but smaller than the positive increase of the first phase.

As seen in FIG. 8, the first time period is shorter than the second time period, is shorter than the third time period and is also shorter than the sum of the second and third time periods, while the third time period is longer than the second time period and is longer than the sum of the first and second time periods.

In another embodiment not shown, the whole period where the step decreases is longer than the period where the first liquid characteristic is more or less constant. In this case, if we suppose the second period to cover more or less the whole decreasing period and the third period to cover more or less the constant period, then the third period is shorter than the second period. If we on the other hand consider the second period to cover only the beginning of the decrease and the third period to cover the rest of the decrease and the whole constant period, then the third period is longer than the second period also in this case. Nonetheless, also in this case we can identify a first relatively short period during which the derivative (or the average variation over time) of the first liquid characteristic is positive, a second period during which such derivative (average variation over time) is "smaller" (with sign), and a third period during which such derivative (average variation over time) is in between.

The first time period can be seen also as a period in which the first liquid characteristic varies in one direction, regarded as positive, from an initial set value (for example 14 mS/cm of conductivity in FIG. 8) to a maximum set value (for example 17 mS/cm).

The altering stage has, after the first time period, a further time period in which the first liquid characteristic decreases (i.e. varies in a negative direction, i.e. in an opposite direction with respect to the variation, regarded as positive, during the first period) directing towards or reaching an essentially flat curve at a constant set value (for example 15 mS/cm) greater than the initial set value.

As seen in FIG. 8, the further time period can be considered more or less the sum of the second and the third time periods, and the first time period is at least twice as short as the further time period.

The initial set value (for example 14 mS/cm of conductivity) is a prescribed treatment value.

According to the altering function, the first liquid characteristic reaches an end set value (for example returning to a steady state with 14 mS/cm of conductivity as in FIGS. 4 to 8), which is also a prescribed treatment value.

In another embodiment (not shown) the first liquid characteristic measurement devices 36, 37 and 38 are not present or are not necessarily used to control the first liquid characteristic according to the altering function. In this embodiment such a control is done directly on the control signal for the speed of the pumps 26, 27 and 28. The procedure consists in having a model for how the conductivity control loop reacts to a change in set point, and then modify the set point change as described by taking into account the normal and the desired responses to the set point change. To do it without using any conductivity cell during the altering stage, the conductivity response to a change in pump speed is pre-stored (this can be done by pre-using a conductivity cell). The change in pump speed is then adjusted in the same way as the set point by using the normal and desired responses.

Thus, in order to speed up the response, the first liquid characteristic (conductivity or other) is not necessarily controlled in a closed loop, but by means of one or more models directly for the response to changes in the pump speed instead of for changes in the conductivity set point.

Moreover, in order to speed up the response we do not even need a second liquid characteristic (conductivity or other) measurement during the treatment of the signal that we want to speed up. It is sufficient to measure this second liquid characteristic during the development of the models (even though this measurement is needed for evaluating at least one patient or treatment or apparatus parameter).

The invention claimed is:

1. A method for determining at least one patient or treatment or apparatus parameter during an extracorporeal blood treatment carried out by an extracorporeal blood treatment apparatus, in which at least a first liquid is circulated towards at least a portion of said extracorporeal blood treatment apparatus, and at least a second liquid flows from said extracorporeal blood treatment apparatus portion, said method comprising:
    altering at least one physical or chemical characteristic of said first liquid according to an altering function determined or predetermined as a function of at least a mathematical model of at least a part of said extracorporeal blood treatment apparatus portion;
    measuring at least one value of at least one physical or chemical characteristic of said second liquid, said second liquid characteristic being changed in response to said alteration of said first liquid characteristic; and
    evaluating at least one patient or treatment or apparatus parameter from at least said at least one measured value of said second liquid characteristic
    wherein said mathematical model comprises a first transfer function that describes a process dynamics of at least a part of said extracorporeal blood treatment apparatus portion, said response to said alteration of said first liquid characteristic being correlated to said process dynamics.

2. The method of claim 1, wherein said first transfer function is a continuous time transfer function or a discrete time transfer function.

3. The method of claim 1, wherein said first transfer function has at least one time constant, said altering function being calculated or precalculated as a function of at least both said first transfer function and a second transfer function having at least one time constant smaller than said time constant of said least one first transfer function.

4. The method of claim 3, wherein said altering function is calculated or precalculated as a function of a compensating function which comprises a quotient of said second transfer function and said first transfer function.

5. The method of claim 4, wherein said altering function is calculated or precalculated as a function of an uncompensated altering function and of said compensating function.

6. The method of claim 5, wherein said uncompensated altering function comprises at least a part in which said first liquid characteristic has an essentially constant set value for a time period.

7. The method of claim 1, wherein said first transfer function comprises at least one low pass filter.

8. The method of claim 1, wherein said first transfer function is of the first order or of an order greater than one.

9. The method of claim 1, wherein said first transfer function contains at least the following expression as a factor:

$$G_f(s) = \frac{1}{1+sT}$$

or $$G(z) = \frac{1-a}{z-a}$$

wherein T and a are two constants.

10. The method of claim 3, wherein said second transfer function comprises at least one low pass filter.

11. The method of claim 3, wherein said second transfer function is of the first order or of an order greater than one.

12. The method of claim 3, wherein said second transfer function contains at least the following expression as a factor:

$$G_s(s) = \frac{1}{1+s\frac{T}{N}}$$

or $$J(z) = \frac{1-\alpha}{z-\alpha}$$

wherein T/N and α are two constants.

13. The method of claim 1, further comprising: selecting or preselecting at least a mathematical model of at least a part of said extracorporeal blood treatment apparatus portion; determining or predetermining said altering function as a function of said selected or preselected mathematical model.

14. The method of claim 1, further comprising:
    pre-storing one or more mathematical models of one or more parts of an extracorporeal blood treatment apparatus in a computer memory;
    identifying at least one part of said extracorporeal blood treatment apparatus portion that is included in said extracorporeal blood treatment apparatus carrying out said treatment;
    associating at least one of said pre-stored mathematical models to said identified part of said extracorporeal blood treatment apparatus portion; and
    determining said altering function as a function of said mathematical model associated to said identified part of said extracorporeal blood treatment apparatus portion.

15. The method of claim 1, wherein said part of said extracorporeal blood treatment apparatus portion comprises at least one volume in a flow system of said extracorporeal blood treatment apparatus portion, said volume slowing down said response to said alteration of said first liquid characteristic.

16. The method of claim 15, wherein said flow system volume comprises a filtering system.

17. The method of claim 16, wherein said filtering system comprises at least one fluid treatment unit, said mathematical model comprising a mathematical model of said fluid treatment unit, said first liquid being a treatment fluid upstream said fluid treatment unit, said second liquid being a treatment fluid downstream said fluid treatment unit.

18. The method of claim 16, wherein said filtering system comprises at least a blood treatment unit, said mathematical model comprising at least one mathematical model of said blood treatment unit, said first liquid being a fresh treatment fluid upstream said blood treatment unit and said second liquid being a spent treatment fluid downstream said blood treatment unit.

19. The method of claim 16, wherein said filtering system comprises at least a blood treatment unit and a fluid treatment unit arranged upstream of said blood treatment unit, said mathematical model comprising a mathematical model of said fluid treatment unit or of said blood treatment unit or of both said units, said first liquid being a treatment fluid upstream said fluid treatment unit, said second liquid being a treatment fluid downstream said fluid treatment unit and upstream said blood treatment unit or a spent treatment fluid downstream said blood treatment unit.

20. The method of claim 1, wherein said first liquid characteristic is the conductivity or at least one ion concentration or the temperature or the density or the viscosity, or an optical parameter like absorbance or transmittance or color, or any parameter reflecting the first liquid composition.

21. The method of claim 1, wherein said second liquid characteristic is the conductivity, or at least one ion concentration, or the temperature, or the density, or the viscosity, or an optical parameter like absorbance (or transmittance) or color, or any parameter reflecting the second liquid composition.

22. The method of claim 1, wherein said altering stage comprises an injection of at least one substance into said first liquid.

23. The method of claim 1, wherein said altering stage is determined as a function of a flow rate of the first liquid.

24. The method of claim 1, wherein said first liquid characteristic alteration is controlled on the basis of a control signal correlated to measured values of said first liquid characteristic or on the basis of at least one prestored operating function of said altering device.

* * * * *

UNITED STATES PATENT AND TRADEMARK OFFICE
CERTIFICATE OF CORRECTION

PATENT NO.         : 7,699,992 B2                                      Page 1 of 1
APPLICATION NO.    : 11/013783
DATED              : April 20, 2010
INVENTOR(S)        : Jan Peter Sternby It is certified that error appears in the above-identified patent and that said Letters Patent is hereby corrected as shown below:

In claim 3, column 21, line 64-65, "said least one," should read --said at least one--.

Signed and Sealed this

Twenty-ninth Day of June, 2010

David J. Kappos
*Director of the United States Patent and Trademark Office*